United States Patent
Ritter et al.

(10) Patent No.: US 10,820,876 B2
(45) Date of Patent: Nov. 3, 2020

(54) METHOD FOR GENERATING IMAGE DATA USING A COMPUTER TOMOGRAPHY DEVICE, IMAGE GENERATING COMPUTER, COMPUTER TOMOGRAPHY DEVICE, COMPUTER PROGRAM PRODUCT AND COMPUTER-READABLE DATA MEDIUM

(71) Applicant: Siemens Healthcare GmbH, Erlangen (DE)

(72) Inventors: Andre Ritter, Neunkirchen am Brand (DE); Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 50 days.

(21) Appl. No.: 16/391,377

(22) Filed: Apr. 23, 2019

(65) Prior Publication Data
US 2019/0336095 A1 Nov. 7, 2019

(30) Foreign Application Priority Data
May 4, 2018 (EP) .................................... 18170877

(51) Int. Cl.
*A61B 6/00* (2006.01)
*G06T 7/11* (2017.01)
(Continued)

(52) U.S. Cl.
CPC ............ *A61B 6/5205* (2013.01); *A61B 6/032* (2013.01); *G06T 7/11* (2017.01); *G06T 11/005* (2013.01);
(Continued)

(58) Field of Classification Search
CPC combination set(s) only.
See application file for complete search history.

(56) References Cited

U.S. PATENT DOCUMENTS

| 2010/0172567 A1* | 7/2010 | Prokoski | ............... | A61B 5/415 |
| | | | | 382/132 |
| 2011/0007959 A1* | 1/2011 | Schulz | ................... | A61B 5/055 |
| | | | | 382/131 |

(Continued)

FOREIGN PATENT DOCUMENTS

DE 102015225395 A1 6/2017

OTHER PUBLICATIONS

Dorn Sabrina et al: "Organ-specific context-sensitive CT image reconstruction and display"; Progress in Biomedical Optics and Imaging; SPIE—International Society for Optical Engineering, Bellingham; WA; US; Bd. 10573; pp. 1057326-1057326; XP060104924; ISSN: 1605-7422, DOI: 10.1117/12.2291897; ISBN: 978-1-5106-0027-0.

(Continued)

*Primary Examiner* — John B Strege
(74) *Attorney, Agent, or Firm* — Harness, Dickey & Pierce, P.L.C.

(57) ABSTRACT

A method is for generating image data using a computer tomography device. CT raw data is provided. An initial image is produced from the CT raw data. The initial image is segmented into regions based upon anatomical features. An image mask corresponding to the regions in each case is produced for the initial image, the image mask defining an effective region for a respectively assigned mapping rule. The mapping rules are applied in the effective regions defined by the respective image masks, and the image data is generated based upon the initial image processed via the mapping rules.

17 Claims, 2 Drawing Sheets

(51) Int. Cl.
*A61B 6/03* (2006.01)
*G06T 11/00* (2006.01)
(52) U.S. Cl.
CPC .............. *G06T 2207/10081* (2013.01); *G06T 2207/20084* (2013.01); *G06T 2211/424* (2013.01)

(56) References Cited

U.S. PATENT DOCUMENTS

| | | |
|---|---|---|
| 2017/0172533 A1 | 6/2017 | Raupach |
| 2017/0273651 A1* | 9/2017 | Behrooz .............. A61B 6/5217 |
| 2019/0216409 A1* | 7/2019 | Zhou ...................... A61B 6/032 |
| 2020/0126271 A1* | 4/2020 | Liang ................... G06T 11/006 |

OTHER PUBLICATIONS

Chen Shuqing et al: "Towards Automatic Abdominal Multi-Organ Segmentation in Dual Energy CT using Cascaded 3D Fully Convolutional Network"; arxiv.org, Cornell University Library, 201 Olin Library Cornell University Ithaca; NY 14853; XP080828979.
European Search Report (EPA Form 1507N) for European Application No. EP18170877.7 dated Oct. 23, 2018.

* cited by examiner

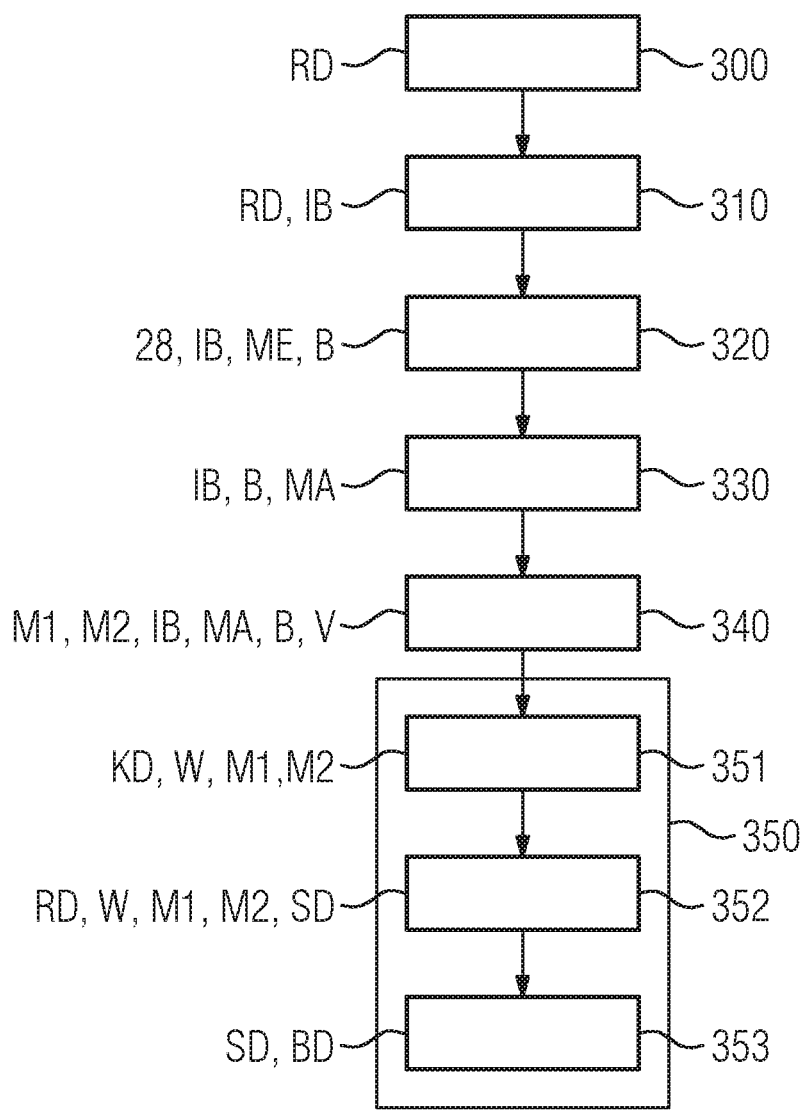

METHOD FOR GENERATING IMAGE DATA USING A COMPUTER TOMOGRAPHY DEVICE, IMAGE GENERATING COMPUTER, COMPUTER TOMOGRAPHY DEVICE, COMPUTER PROGRAM PRODUCT AND COMPUTER-READABLE DATA MEDIUM

PRIORITY STATEMENT

The present application hereby claims priority under 35 U.S.C. § 119 to European patent application number EP 18170877.7 filed May 4, 2018, the entire contents of which are hereby incorporated herein by reference.

FIELD

Embodiments of the invention generally relate to a method for generating image data using a computer tomography device; an image generating computer comprising a controller for performing the method; and a computer tomography device comprising such an image generating computer.

BACKGROUND

A computer tomography device (CT device) is often used for the purpose of generating image data for medical diagnoses and for the planning of therapies. For this, the image data is generated, in particular reconstructed, from CT raw data that has been recorded via the CT device, and is used in the form of a sectional view or as a three-dimensional volume view of the examined object, typically a patient. In this case, an amount of a specific material property is depicted by (image) values of the image data. In particular, a respective image value is assigned to each pixel or to a voxel. In the context of medical diagnosis, in particular, an amount of an absorption coefficient, on the basis of which it is possible to distinguish or examine structures in the scanned region of the object, corresponds to the respective image value.

Furthermore, such image data is used in the planning of a radiation therapy. It is intended here to predetermine as accurately as possible a localized distribution of radiation doses which is applied to the patient during the course of the radiation therapy, in order to preserve non-malignant tissue and/or to apply a radiation dose which is suitable for therapy to malignant tissue. If irradiation with e.g. photons is performed, this produces an interaction of the received radiation and consequent secondary processes, in particular with electrons. A charge density distribution, in particular an electron density distribution, is therefore used in an appropriate manner as image data for the radiation therapy.

The image data generated from the CT raw data can show (image) artifacts such as e.g. beam hardening artifacts, which occur during the recording of the CT raw data due to the use of polychromatic X-radiation, or also saturation artifacts. These artifacts disadvantageously make a reliable diagnosis more difficult or make it harder to plan the therapy, since the image value does not correspond to the amount of the material property of an (anatomical) structure assigned to the image value, and consequently the (anatomical) structure appears to be blurred or distorted.

Use is conventionally made of (reconstruction) methods which use a threshold value in order to correct the image data. For example, DE 10 2015 225 395 A1 discloses a method for determining a spatial distribution of a material property value. In this, provision is made for first reconstructing image data on the basis of measured projection data. Image points of the image data are then classified using a threshold value and a distribution of two base materials is estimated according to the classification. A spatial distribution of the material property values is determined using the estimated distribution and the measured projection data.

Methods which make use of threshold-based correction are disadvantageous in that different materials are comparatively difficult to distinguish if they are represented by similar image values and/or if the different materials have an overlapping distribution. For example, it is comparatively difficult to distinguish between bones and a contrast medium. Moreover, a distribution of the material properties represented by image values might not correspond to the actual distribution in the object due to artifacts, for example. However, if a correction of the image data is based on the assumption that the segmented regions correspond to the actual distribution in the object, errors can then occur in the correction.

SUMMARY

At least one embodiment of the invention allows an improvement in the quality of image data which is reconstructed from CT raw data. In particular, artifacts should be prevented or at least reduced in this way.

At least one embodiment of the invention is inventively achieved by a method for generating image data. In addition, at least one embodiment of the invention is inventively achieved by an image generating computer. Furthermore, at least one embodiment of the invention is inventively achieved by a computer tomography device.

According to the method of at least one embodiment, a method for generating image data using a computer tomography (CT) device comprises
  providing CT raw data;
  producing an initial image from the CT raw data;
  segmenting the initial image into regions based upon anatomical features;
  producing a respective image mask for the initial image, for each of the regions, each respective image mask defining an effective region for a respectively assigned mapping rule;
  applying respectively assigned mapping rules in respective effective regions defined by respective image masks; and
  generating the image data based upon the initial image processed by the mapping rules.

A suitable image generating computer (reconstruction computer) has a controller which is configured to perform an embodiment of the method described above. The controller is e.g. an FPGA (field programmable gate array) or an ASIC (application specific integrated circuit) or comprises such an FPGA or ASIC.

The image generating computer appropriately has a computer-readable medium (data medium) or additionally or alternatively the computer-readable medium can be linked to the image generating computer, in particular for data communication purposes.

At all events, the computer-readable medium comprises a computer program product including program code which is designed as an image generating program, wherein the method in one of the variants described above is performed when the image generating program is executed by the controller. The neural network for performing the segmentation is e.g. part of the image generating program. Alternatively, the image generating program has an interface to the neural network. In summary, the image generating computer is therefore so configured as to produce an initial image from CT image data that has been provided, and to segment and mask the initial image in order to generate image data.

In an advantageous embodiment, a computer tomography device comprises the image generating computer described above. Therefore the image generating computer and the computer tomography device analogously have the features and advantages arising from the method described above.

In summary, the inventive computer program product of an embodiment, in particular the image generating program described above, therefore has program code (i.e. in particular corresponding instructions) for performing an embodiment of the method described above when the computer program product is executed on a computer (in particular on the image generating computer described above or by the controller thereof). In this case, an embodiment of the inventive computer program product is stored on an embodiment of the inventive data medium and is therefore comprised therein.

BRIEF DESCRIPTION OF THE DRAWINGS

Example embodiments of the invention are explained in greater detail below with reference to a drawing, in which:

FIG. 3 shows a schematic sequence diagram of an alternative example embodiment of the method from FIG. 2, wherein correction data for generating the image data is determined from the processed initial image.

DETAILED DESCRIPTION OF THE EXAMPLE EMBODIMENTS

Figure 1:
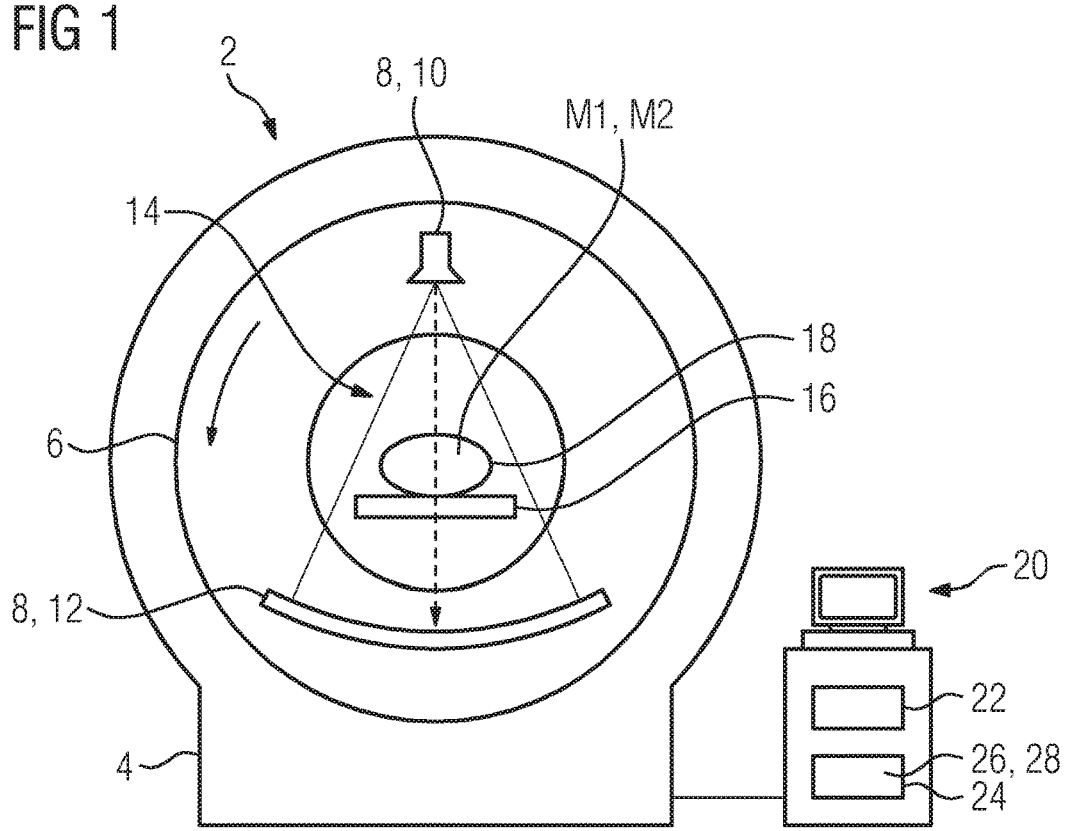
FIG. 1 shows a schematic front view of a computer tomography device with an image generating computer.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the inventive method is designed to generate image data using a computer tomography device. In this case, the image data has (image) values which represent a material property in particular. The image data is e.g. a depiction of the spatial distribution of iodine (iodine image) as a contrast medium, an absorption coefficient (absorption image) representing the absorptance of X-radiation, or a charge density, e.g. the nuclear charge number.

According to the method of at least one embodiment, CT raw data (CT recorded data) of an examination region, i.e. the region that is scanned during the recording of the CT raw data, of an object that is to be examined, e.g. a patient, is provided first in this case. An initial image is then produced from this CT raw data, wherein e.g. an iterative reconstruction as disclosed in the prior art or preferably the so-called filtered back projection is used for this purpose.

Following thereupon, the initial image is segmented into regions on the basis of anatomical features and, for each of these regions, an image mask corresponding to the region in each case is produced for the initial image. An anatomical feature in this case is a property of an (anatomical) structure, e.g. a bone, an organ, vessels, nerve fibers or an implant, by which property this structure can be and is distinguished from a further structure in the initial image. In particular, this property is the shape (form), the surface, the position, the relative position of this structure to the further structure or a structuring of the structure, e.g. a specific arrangement of vessels or glands. For example, for the purpose of segmentation, use is made of a threshold value in addition to the anatomical features, in particular the shape or the position of the corresponding structure. However, such structures can also be distinguished from each other in particular if their respective absorption coefficients differ sufficiently, taking any image noise into account. Knowledge of an (absolute) amount of the absorption coefficient of the corresponding structure is therefore unnecessary in this context, though it is necessary in the case of a segmentation based on a predetermined threshold value. The (segmented) regions in this case preferably correspond to the anatomical structure or the shape thereof. Alternatively, for example, the region is dimensioned to be larger or smaller as a function of the structure or the type of structure.

In this case, each of the image masks defines an effective region of the initial image for a mapping rule assigned to this image mask. Therefore the mapping rule is effective only in that region of the initial image which is assigned to the corresponding image mask, i.e. covered by the image mask. The image masks are preferably separate from each other, i.e. they have no common effective regions and do not intersect each other.

A mapping rule, also referred to as a method rule or mapping function, is or comprises in particular a mathematical function in this case. This mathematical function is preferably based on a physical or statistical model or is derived from the model. The image values of the initial image in the corresponding effective region form the independent variables of the mathematical function in this case. In other words the image values are processed, i.e. specified and possibly changed, via the mapping rule. In this case, the mapping function is e.g. a sectionally linear function which is defined on a subinterval or a plurality of subintervals of the positive value space. Alternatively, the mapping function is or comprises a convolution or a filter function for processing the image values, by which filter function image quality parameters of the image data, e.g. a noise or an image sharpness, are processed accordingly.

Alternatively or additionally, the mapping rule is a mathematical operation in particular, e.g. an assignment of the image values or a portion of the image value to a class, in particular to a (base) material.

A plurality of mapping rules are applied to a region, for example.

According to at least one embodiment of the method, the mapping rules are then applied in the effective regions defined by the corresponding image mask. In other words, the effective regions defined by the image masks are processed via the respectively assigned mapping function, this being also referred to as "masking" below.

In a further step, the image data is generated on the basis of the initial image thus processed by the mapping rules.

If artifacts are present, segmentation of the initial image on the basis of anatomical features is advantageously prone to comparatively little error, in particular in comparison with a segmentation which is based on a threshold value. On the basis of the initial image which has been segmented with reference to anatomical features or on the basis of the corresponding regions, also referred to simply as segmented regions below, it is therefore advantageously possible to determine and/or generate the image data free of artifacts or at least with fewer artifacts.

For example, by means applying the mapping functions to the corresponding regions, a bone image is extracted from the initial image by extracting from the initial image, and using as image data, only those regions to which the anatomical feature of the corresponding bone are assigned.

According to an advantageous development, the segmented regions are in each case assigned a multi-material base comprising a corresponding number of (base) materials in accordance with the respective anatomical features. Therefore a spatial distribution of an absorption coefficient (attenuation coefficient), which is represented in particular by the image values of the initial image, is depicted here as a linear continuity, i.e. by a sum of products. In this case, each of the products has as one factor the spatial distribution of the contribution of the respective base material to this spatial distribution of the absorption coefficient, and as another factor the (linear) absorption coefficient of the corresponding base material, this being dependent on the energy of the X-radiation. In other words, for each of the materials, the products have a factor depicting the spatial distribution thereof and a factor depicting the energy-dependent absorption coefficient thereof.

In this case, the spatial distribution of the contributions of the base materials to the spatial distribution cannot in general be definitively specified solely on the basis of the distribution of the absorption coefficient, which is represented in particular by the image values of the initial image. For example, for a given image value, it cannot be definitively specified whether the material bone or the materials soft tissue and contrast medium give rise to the image value, or in what proportions the respective material contributes to the image value.

In particular, a density change in the anatomical structure, assuming a constant ratio (composition ratio, density ratio) of the base materials in the structure and therefore in particular also assuming a constant ratio of the spatial distribution of the contributions of the corresponding materials to the spatial distribution of the absorption coefficient, causes a proportional change of the absorption coefficient and a corresponding change of the image values. In another anatomical structure comprising these materials, but in another ratio of the spatial distribution of the contributions of the materials to the spatial distribution of the absorption coefficient, an analogous density change will produce a proportional change of the absorption coefficient but with a different proportionality factor. Therefore the changes in the absorption coefficient of the two anatomical structures differ in the case of an analogous density change. In particular, for this reason, a suitable multi-material base is assigned to an anatomical structure and a suitable mapping rule is selected accordingly.

In summary, for a predetermined spatial distribution of the absorption coefficient, the spatial distribution of the contributions of the base materials cannot be definitively specified and a plurality of ratios (composition ratios, density ratios) are possible.

By virtue of the segmentation based on anatomical features, the scope (a number) of all possible ratios of the spatial distributions of the contributions of the corresponding base materials to the respective image value, which corresponds to the spatial distribution of the absorption coefficient as represented by the image values and specified from the CT raw in particular, is restricted to a comparatively significant extent or the spatial distribution of the contributions can even be specified exactly. In particular, the scope of all possible absorption coefficient distribution ratios (composition ratios, density ratios) of the materials of the correspondingly assigned region is therefore restricted (reduced) or even specified exactly by virtue of the segmentation based on anatomical features. By way of the spatial distribution thus specified of the contributions of the corresponding base materials to the respective image value, the spatial distribution of these materials can advantageously be estimated comparatively accurately or even specified exactly.

For medical applications, e.g. water as a first material and bone as a second material are suitable as a multi-material base for a region assigned to a bone. For a region assigned to a soft tissue, a suitable multi-material base is formed by the materials water and contrast medium, in particular iodine.

For medical applications, fatty tissue is also suitable as a base material. If only one material is present in one of the segmented regions or if this region is assigned only one material, e.g. a metal for a region to which an implant is assigned as an anatomical feature, this material is suitable as a single-material base for the corresponding region. To this extent, a multi-material base is understood to signify a single-material base also.

For example, as part of this activity, these materials are also approximated by suitably selected materials, in particular having known properties. Therefore bone can be approximated by calcium, or soft tissue by water. In particular, by way of a suitable selection of the base materials for the multi-material base, their physical properties in respect of the imaging, e.g. the dependence of their attenuation coefficient on the energy of the X-radiation used to record the CT raw data, and the physiology of the corresponding anatomical structure are taken into account.

The multi-material base is preferably designed as a two-material base. In other words, a base material analysis takes place on the basis of two materials. As a result of this, the scope of all possible distributions of the contributions of the base materials to the corresponding image value, based on the segmentation with reference to anatomical features, is advantageously smaller than in the case of a multi-material base with more than two base materials.

According to an appropriate development, the assignment or specification of the contributions of the corresponding (base) materials to the image values is performed with the aid of the mapping function in this case. For example, by the mapping function, a material of the multi-material base having an increasing image value is assigned a correspondingly linearly increasing contribution to the image value. In summary, the image values are processed by the mapping rule and, in addition, the contributions to the corresponding image value are assigned to the corresponding materials by the mapping rule. Likewise in summary, the regions are evaluated by the corresponding mapping rule in respect of the respective (base) materials which are present in the corresponding region.

It is thereby advantageously possible to determine image data which represents the spatial distribution of only one of the materials, all of the materials or a subgroup of the materials. For example, in a region to which soft tissue is assigned, a contribution to the image value by the soft tissue and by a contrast medium is specified by way of a suitably selected mapping function. The spatial distribution of the contrast medium is determined therefrom. The spatial distribution of the contrast medium, in particular iodine, is then used to generate the image data and is depicted as a so-called iodine image. Alternatively, image data is generated on the basis of those contributions, or the distribution thereof, which were not assigned to the contrast medium by the mapping rule, such that the image data depicts a native image, i.e. the depiction of the spatial distribution of the attenuation coefficients without the corresponding contributions from the contrast medium. Alternatively, for example, a so-called water image is generated analogously and represents the spatial distribution of the material water.

On the basis of the determined distribution of the materials, and knowing the dependence of their absorption coefficient on the energy of incident X-radiation, it is further possible to generate image data whose image values correspond to a CT recording made with an (in particular monochromatic) X-radiation energy that is predetermined by a user.

According to an advantageous embodiment, the mapping rule is selected as a function of the anatomical feature assigned to the corresponding region or the multi-material base which is assigned correspondingly. In this way, it is advantageously possible to select different mapping rules for different multi-material bases or anatomical features. The mapping rule is therefore dependent on the multi-material base assigned to the respective region or on the anatomical feature. In particular, contributions to the corresponding image values are thereby assigned to the corresponding (base) materials in a comparatively precise manner. Consequently, an estimation of the spatial distribution of the contributions of the (base) materials to the distribution of the absorption coefficient, this being represented by the image values in particular, and hence a corresponding spatial distribution of these materials, is further improved.

According to an advantageous development of the method, as an alternative or in addition to specifying the image data from the masked regions in one of the variants described above, correction data is first generated from the masked regions, preferably from every masked region. This is then used to specify corrected image data, in particular image data having fewer artifacts.

In order to achieve this, for example, the spatial distributions of the materials are initially specified in one of the variants described above by applying the mapping rules and the associated assignments of the respective contributions to image values of the initial image to the corresponding material. By way of a forward projection of these distributions into the so-called projection space, an (effective) path length for the in particular polychromatic X-radiation that is used for the recording of the CT raw data is then determined in each case for these materials. On the basis of the determined path lengths of the materials and on the basis of the CT raw data, the effective path length of one of these materials, in particular water, is corrected or alternatively specified. By way of the corrected effective path length of this material and the effective path lengths of the other materials, line integrals or (artificial, synthetic) CT (projection) data, also referred to as corrected CT raw data, is then specified via a convex combination, for example. This data is then transferred into the image space by generating the image data.

In summary, on the basis of the distribution that has been determined in respect of the materials, correspondingly corrected path lengths are determined. Synthetic CT data which is produced by way of these corrected path lengths and is converted into image data therefore contains no artifacts or comparatively few artifacts, or artifacts of comparatively weak definition.

The assignment of the multi-material base to the corresponding region or to the corresponding anatomical structure and the generation of the corresponding (corrected) image data most preferably take place automatically. This means that errors due to manual input by a user, e.g. during the selection of the base materials, are avoided and artifacts, in particular beam hardening artifacts, are avoided or at least reduced due to the automatic selection of the base materials and the correction data which is generated correspondingly.

According to a suitable embodiment of the method, the specification of the corrected image data takes place iteratively on the basis of correction data that is generated. In other words, the corrected image data is determined or generated via iteration by applying the correction data.

According to a first variant embodiment of the iterative specification of the corrected image data, use is made of a so-called iterative reconstruction. In particular, a regularization takes place as a function of the correction data in this case, and is applied during the course of the iterative reconstruction. The correction data here represents e.g. the assignment to a segmented region or to the assigned anatomical structure or to one of the materials of the multi-material base. The regularization then takes place as a function of this assignment, in particular a corresponding mathematical function for the regularization is selected as a function of the assignment. By way of the regularization here, for example, the image sharpness in a region assigned to the anatomical structure "bone" is increased and image noise in a region assigned to the anatomical structure "water" or "soft tissue" is reduced.

Alternatively, according to a second variant embodiment of the iterative specification of the corrected image data, the method described above for generating image data or sub-steps of the method form an iteration step of the iteration. In this context, the iteration step (iteration loop, iteration stage) of the iteration comprises e.g. the segmentation based on anatomical features, the masking of the initial image of this iteration step, the determination of correction data and the application of the correction data for the purpose of generating image data, which in turn is used to produce an initial image of the next iteration step. Alternatively, an iteration step of the iteration comprises only the masking, the determination of correction data and the application of the correction data for the purpose of generating the initial image of the next iteration step, wherein the image masks were specified before the iteration by way of the segmentation based on anatomical features and these masks are used for all iteration steps. The iteration therefore comprises at least one and preferably a plurality of iteration steps. A break condition for the iteration can be, for example, the number of iteration steps or a degree of similarity between a predetermined model of the anatomical structure and the anatomical structure according to the image data.

According to an appropriate variant embodiment of the method, the correction data and the CT raw data are used to specify an electron density distribution, i.e. a spatial distribution of the electron density, as image data. In particular, the spatial distribution of the electron density is used for the planning of radiation therapy. For this, e.g. the image values corresponding to an absorption coefficient, the image values being presented in the Hounsfield scale, are converted into an electron density by way of a known function or by way of a known conversion table. Provision is preferably made here for converting the image values of the CT raw data that was corrected by the correction data. This procedure can be applied analogously for the purpose of specifying the spatial distribution of a nuclear charge number.

In particular, as a result of the segmentation based on anatomical features and the processing by the mapping function, the processing preferably being dependent on the selection of the assigned multi-material base, a spatial distribution of the electron density which is free of artifacts or at least has fewer artifacts can be and is specified. This allows improved irradiation planning, making it possible in particular to specify a distribution of a radiation dose that will be received in the patient.

According to a suitable embodiment, an (artificial) neutral network is used to segment the initial image. The neural network in this case is preferably a so-called "convolutional neural network", in particular a "deep convolutional neural network". Such neural networks are trained and recognize general associations or patterns. In other words, the data used to train the neural network is not only learned from memory. As a result, such neural networks are advantageously comparatively robust in the face of anatomical variations and/or a variation in the addition of iodine in the assigned tissue, i.e. the initial image is reliably and correctly segmented on the basis of the anatomical features even in the case of such variations and/or if artifacts are present in the initial image.

For the purpose of training the neural network, use is made of e.g. CT raw data or image data from medical CT examinations which have actually been performed. Alternatively or additionally, use is made of data that is generated via simulation. For example, this data is produced in a simulation. In particular, contrast enhancements in previously known initial images are calculated for this purpose, wherein the segmentation based on anatomical features of the initial images is already known. For example, such a neural network is trained to distinguish between bone and soft tissue on the basis of the anatomical features, in particular irrespective of a contrast medium that may be present, and to segment the initial image into regions accordingly.

Additionally or alternatively, such a neural network is trained such that vessels to which a contrast medium has been added can be distinguished from bone for the purpose of the corresponding segmentation. Moreover, in addition or alternatively, such a neural network is trained to recognize implants on the basis of their shape and/or position. The segmentation of such implants makes it possible to generate correction data by which metal artifacts due to the implant can be reduced or prevented.

As an alternative to using a neural network, use is made of a model-based method in which a volume model of the structure to be segmented, e.g. an organ or a bone, is adapted in accordance with the measured image values. Here, the adaptation of the volume model takes place in particular as a function of a variable which represents a similarity or correlation between the volume model, the anatomical structure underlying the segmentation and/or the image values.

According to an appropriate embodiment, the CT raw data is provided in the form of projection image data. The projection image data comprises a sinogram in this case. This represents an intensity profile of incident X-radiation on an (X-ray) detector for a corresponding (recording) angle. The projection image data preferably also comprises information relating to a recording geometry, i.e. a relative arrangement between the detector, an (X-ray) source which generates the X-radiation, and the examined object, in particular the recording angle. The projection image data is captured and provided via the computer tomography device in particular. Alternatively, the projection image data is loaded from a database. If only previously reconstructed image data is stored in a database, this can be converted into CT raw data by way of a forward projection in order to perform the method and thereby advantageously to avoid artifacts.

In summary, by a suitable selection of the mapping rule, it is possible to generate image data according to a predetermined purpose. The image data can therefore represent e.g. a spatial distribution of a contrast medium, an absorption coefficient or a charge density, e.g. the nuclear charge number or in particular the electron density. Alternatively or additionally, by a suitable selection of the mapping rule, it is possible selectively to change an image quality parameter in the corresponding regions, e.g. an image noise.

A suitable image generating computer (reconstruction computer) has a controller which is configured to perform the method described above. The controller is e.g. an FPGA (field programmable gate array) or an ASIC (application specific integrated circuit) or comprises such an FPGA or ASIC. The image generating computer appropriately has a computer-readable medium (data medium) or additionally or alternatively the computer-readable medium can be linked to the image generating computer, in particular for data communication purposes. At all events, the computer-readable medium comprises a computer program product including program code which is designed as an image generating program, wherein the method in one of the variants described above is performed when the image generating program is executed by the controller. The neural network for performing the segmentation is e.g. part of the image generating program. Alternatively, the image generating program has an interface to the neural network. In summary, the image generating computer is therefore so configured as to produce an initial image from CT image data that has been provided, and to segment and mask the initial image in order to generate image data.

In an advantageous embodiment, a computer tomography device comprises the image generating computer described above. Therefore the image generating computer and the computer tomography device analogously have the features and advantages arising from the method described above.

In summary, the inventive computer program product of an embodiment, in particular the image generating program described above, therefore has program code (i.e. in particular corresponding instructions) for performing an embodiment of the method described above when the computer program product is executed on a computer (in particular on the image generating computer described above or by the controller thereof). In this case, an embodiment of the inventive computer program product is stored on an embodiment of the inventive data medium and is therefore comprised therein.

FIG. 1 shows a computer tomography device 2. This comprises a retaining frame 4 for an annular slewing ring 6 which is also referred to as a gantry. The slewing ring 6 is rotatably mounted on the retaining frame 4 in this case. The slewing ring 6 supports an X-ray system 8 comprising an X-ray source 10 for generating X-radiation and, positioned opposite this, an (X-ray) detector 12 for the X-rays. The X-radiation generated by the X-ray source 10 has a spectral distribution in this case. In other words, the X-radiation is polychromatic.

A patient couch 16 can be moved in and out of the tunnel-shaped recording region 14 (examination tunnel) which is formed by the annular slewing ring 6. In order to capture (record) CT raw data RD, an examination object 18, in particular a patient, is placed on the patient couch 16 and moved into the recording region 14. As the slewing ring 6 rotates, the X-ray system 8 circulates around the object 18 situated on the patient couch 16. As a consequence, the CT raw data RD of the object 18 is recorded from different angles (spatial angles, recording angles), wherein the CT raw data RD represents an intensity profile of the incident X-radiation at the corresponding (recording) angles or for the corresponding recording geometry. The CT raw data RD is produced as projection image data in this way.

In addition to this, the object 18 or the patient has different anatomical structures, e.g. an organ, a bone or fatty tissue, in the examined region, i.e. the region (examination region) that is captured by the CT raw data RD.

In order to capture the CT raw data RD that is captured by the detector 12 and to control the X-ray system 8, the latter is connected to a reconstruction computer 20 for signal transmission purposes. The reconstruction computer 20 in this case has a controller 22 and a computer-readable medium 24 (computer-readable data medium 24) in the form of a fixed disc, on which is stored a computer program product 26 comprising an image generating program and a neural network 28. When the image generating program is executed by the controller 22, a method for generating image data BD is performed as described in FIG. 2 and FIG. 3 and in the following.

Figure 2:
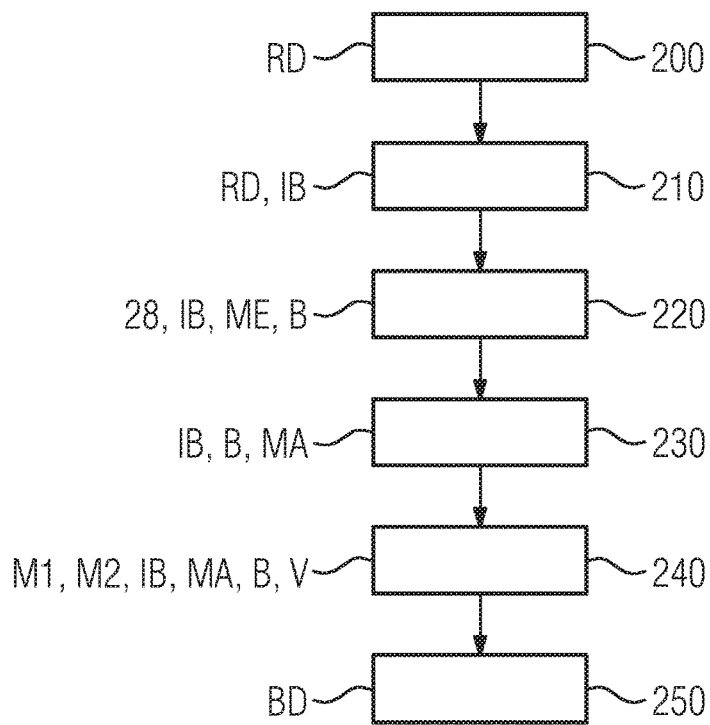
FIG. 2 shows a schematic sequence diagram of a method for generating image data from CT raw data, the method being performed by the computer tomography device, wherein an initial image produced from the CT raw data is processed by way of mapping rules.

FIG. 2 shows a first embodiment of the method for generating image data BD. In this method, the CT raw data RD in the form of projection image data is provided in a first step 200. In a second step 210 following thereupon, an initial image IB is produced from the CT raw data RD, in particular via the filtered back projection.

In a third step 220, the initial image IB is segmented into regions B on the basis of anatomical features ME. In particular, an anatomical structure, e.g. an organ such as the liver or a bone, the arrangement thereof relative to a further anatomical feature, or the shape thereof are used as anatomical features ME. In this case, the regions B correspond to the respective anatomical structure or the shape thereof. For the purpose of segmentation, use is made of a neural network 28, in particular a so-called "convolutional neural network", preferably a "deep convolutional neural network". This is trained, for example, to distinguish between bone and soft tissue on the basis of the anatomical features ME, in particular irrespective of a contrast medium that may be present, and to segment the initial image IB into regions B accordingly.

In a fourth step 230 following thereupon, an image mask MA, also referred to as mask MA, corresponding to the regions in each case is produced for the initial image IB. These define in each case an effective region of the initial image IB, in which a mapping rule V (mapping function) assigned to the image mask MA is effective, i.e. applied.

In the fifth step 240, the mapping rules V are applied in the effective regions defined by the image masks MA. Here, the (segmented) regions B are in each case assigned a two-material base comprising the (base) materials M1 and M2 according to the respective anatomical features ME. The initial image IB is divided into two regions B here. In this case, the second region B corresponds to the anatomical structure of a bone of the patient and the first region B corresponds to the anatomical structure of a soft tissue surrounding the bone. Furthermore, the first of the two regions B is assigned a multi-material base in the form of a two-material base comprising the (base) materials M1 and M2 contrast medium and soft tissue respectively, the latter being approximated by water. It is therefore taken into account when selecting the two-material base that, by definition, bone is not present as a further material in an anatomical structure "soft tissue". The second of the two regions B is assigned a two-material base in the form of a two-material base comprising the materials M1 and M2 bone and water respectively. In the second region B here, a contribution resulting from a contrast medium is assumed to be zero, since this occurs in only negligible concentration in the anatomical structure "bone".

The image values of the regions B of the initial image IB are evaluated by the respective mapping rule V in respect of the corresponding materials M1 and M2, in other words the contributions of the materials M1 and M2 to the corresponding image value of the initial image IB are specified. The mapping rules V in this case are dependent on the respective two-material base, i.e. the two regions B are processed differently by the corresponding mapping rule V. In this case, the mapping rules V are mathematical functions which, with the image values as free variables of the function, specify the contributions to this image value by the materials M1 and M2 in each case, and an associated mathematical operation, which assigns the specified contributions to the corresponding material M1 and M2 of the corresponding region B. On the basis of this assignment and the specified contributions, a distribution of the materials M1 and M2 in the respective regions B is then specified.

According to this example embodiment, the mapping rules V differ in this case as a function of the respectively assigned two-material base. Therefore for the first region B, the contributions to the image value are specified and assigned on the basis of the contrast medium as material M1 and on the basis of water as material M2. A contribution based on bone as a further material in this region B is always assumed to be zero in accordance with the selected two-material base, and therefore the mapping function V does not assign any contribution based on bone to the image value. For the second region B, the contributions to the image values based on bone as material M1 and based on water as material M2 are correspondingly specified and assigned analogously. A contribution based on a contrast medium is assumed to be zero in accordance with the selected two-material base. On the basis of the specification of the contribution to the image values and the corresponding assignment to the material contrast medium, and with reference to the known position of the pixel or voxel assigned to the corresponding image value, a spatial distribution of the contrast medium is specified. The image data BD is generated from this distribution in a sixth step 250. The image data BD here takes the form of a contrast medium image, which shows the spatial distribution of the contrast medium in the examined region of the object 18. Additionally or alternatively, the image data BD analogously takes the form of a bone image, i.e. the spatial distribution of the material bone as specified by the mapping rule. In summary, according to this variant of the method, image data BD is therefore generated which shows the distribution of one of the materials M1 or M2.

In an alternative (not further illustrated) of the method according to FIG. 2, in the fifth step 240 the mapping rules V are applied in the effective regions defined by the image masks MA, the other steps being performed analogously. The mapping rule V here is not dependent on the anatomical feature ME assigned to the corresponding region or on the correspondingly assigned multi-material base. For example, the mapping rule V is a filter function which assigns the value zero to image values below a threshold value. In an alternative embodiment, a noise is reduced or an image sharpness in increased by the mapping rule. At all events, the corresponding effective regions are processed via this filter function and the image data BD is generated in the sixth step 250 from the initial image IB processed thus.

FIG. 3 shows a further alternative embodiment of the method for generating image data BD. In this case, the steps 300 to 340 inclusive take place analogously to the steps 200 to 240 of the embodiment in FIG. 2 and are therefore not described further. On the basis of the distribution of the materials M1 and M2 specified in the step 340, namely water, bone and iodine as a contrast medium here, correction data KD (substep 351 of the step 350) is generated first. According to this example embodiment, for this purpose, the spatial distribution of each of the materials M1 or M2 in all regions B is transferred via a forward projection into the so-called projection space and, for each of the materials M1 and M2, (effective) path lengths W of the polychromatic X-radiation that is used to record the CT raw data RD and the corresponding recording geometry are determined in each case.

On the basis of the determined path lengths W of all materials M1 and M2 and on the basis of the CT raw data RD, the effective path length W of a material M1 or M2 is corrected or determined (substep 352 of the step 350). Here, by way of the CT raw data and by way of the specific path lengths W of the materials bone (material M1 in the first region) and contrast medium (material M1 in the first region), the path length W of the material water (material M1) is specified or the path length W specified in step 351 for water (material M1 in the second region and material M2 in the first region) is corrected.

By way of the corrected path length W of the material water and by way of the path lengths W of the other materials M1 and M2, i.e. contrast medium and bone, synthetic CT (projection) data SD is generated via a so-called convex combination. Furthermore, the image values here are converted into an electron density via a known function or via a known conversion table. In substep 353 of the step 350, the image data BD representing the electron density is generated from this synthetic CT data SD via back projection. In summary, this alternative embodiment therefore generates image data BD which represents a corrected electron density distribution of all materials M1 and M2.

In a variant embodiment (not further illustrated) of the method according to FIG. 3, the specification or the generation of the corrected image data BD takes place iteratively. In this case, the steps 310 to 352 represent iteration steps, i.e. an iteration sequence, of an iteration. The synthetic CT data SD generated in substep 352 is used to generate the initial image IB of the next iteration step.

In a further variant embodiment (not illustrated) of the method according to FIG. 3, the steps 300 to 340 take place analogously, but step 350 differs as described below. In a first substep 351 of the step 350, correction data KD is generated. The correction data KD here represents the assignment to a segmented region B or to one of the materials M1 or M2 of the multi-material base. In a second substep 352 of the step 350, the correction data KD is then used for an iterative reconstruction. A regularization which is applied during the course of the iterative reconstruction therefore takes place as a function of the correction data KD. The regularization therefore takes place as a function of this assignment. By way of the regularization, when the image data BD is generated as a result of the iterative reconstruction based on the correction data, the image sharpness in a region B assigned to the anatomical structure "bone" is increased and an image noise in a region B assigned to the anatomical structure "water" or "soft tissue" is reduced.

The invention is not restricted to the example embodiments described above. Rather, other variants of the invention can also be derived therefrom by a person skilled in the art without thereby departing from the scope of the invention. In particular, all of the individual features described in connection with the example embodiments can also be combined together in other ways without thereby departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating image data using a computer tomography device, comprising: providing CT raw data; producing an initial image from the CT raw data; segmenting the initial image into regions based upon anatomical features; producing a respective image mask for the initial image, for each of the regions, each respective image mask defining an effective region for a respectively assigned mapping rule; applying respectively assigned mapping rules in respective effective regions defined by respective image masks; and generating the image data based upon the initial image processed by the mapping rules, wherein the regions segmented are each assigned a multi-material base comprising materials according to a respective anatomical feature, and wherein a spatial distribution of the materials of a respective multi-material base is determined via a corresponding mapping rule wherein in determining the spatial distribution of the materials of the respective multi-material base, a contribution of the materials to corresponding image values of the initial image is specified, in each case, via the mapping rule.

2. The method of claim 1, wherein the mapping rule is selected as a function of the anatomical feature assigned to a corresponding region or a multi-material base correspondingly assigned.

3. The method of claim 2, wherein, in determining a spatial distribution of materials of a respective multi-material base, a contribution of the materials to corresponding image values of the initial image is specified, in each case, via the mapping rule.

4. The method of claim 1, wherein correction data for specifying corrected image data is generated based upon the regions processed via the corresponding mapping rule.

5. The method of claim 4, wherein the corrected image data is iteratively specified based upon the correction data.

6. The method of claim 5, wherein in generating the image data, use is made of an iterative reconstruction in which regularization takes place as a function of the correction data.

7. The method of claim 5, wherein an iteration step of an iteration includes at least the application of the mapping rules, the generation of the correction data and the generation of corrected image data.

8. The method of claim 4, wherein an electron density distribution is specified as image data based upon the correction data and the CT raw data.

9. The method of claim 1, wherein a neural network is used in segmenting the initial image.

10. The method of claim 9, wherein a deep convolutional neural network is used in segmenting the initial image.

11. The method of claim 1, wherein the CT raw data is provided as projection image data.

12. A non-transitory computer program product, storing program code for performing the method for image generation of claim 1 when the computer program product is executed on a computer.

13. A non-transitory computer-readable data medium storing program code for performing the method for image generation of claim 1 when the program code is executed on a computer.

14. The method of claim 1, wherein the mapping rule is selected as a function of the anatomical feature assigned to a corresponding region or a multi-material base correspondingly assigned.

15. The method of claim 1, wherein correction data for specifying corrected image data is generated based upon the regions processed via a corresponding mapping rule.

16. An image generating computer, comprising: a controller configured to produce an initial image from computed tomography (CT) raw data, segment the initial image into regions based upon anatomical features, produce a respective image mask for the initial image, for each of the regions, each respective image mask defining an effective region for a respectively assigned mapping rule, apply respectively assigned mapping rules in respective effective regions defined by respective image masks, and generate the image data based upon the initial image processed by the mapping rules, wherein the regions segmented are each assigned a multi-material base comprising materials according to a respective anatomical feature, and wherein a spatial distribution of the materials of a respective multi-material base is determined via a corresponding mapping rule wherein, in determining the spatial distribution of the materials of the respective multi-material base, a contribution of the materials to corresponding image values of the initial image is specified, in each case, via the mapping rule.

17. A computer tomography device, comprising the image generating computer of claim 16.

* * * * *